(12) United States Patent
Janssens

(10) Patent No.: US 9,237,906 B2
(45) Date of Patent: Jan. 19, 2016

(54) COMBINATION OF A BONE DRILL AND A SLEEVE

(76) Inventor: Johan Janssens, Antwerp (BE)

( * ) Notice: Subject to any disclaimer, the term of this patent is extended or adjusted under 35 U.S.C. 154(b) by 0 days.

(21) Appl. No.: 13/541,968

(22) Filed: Jul. 5, 2012

(65) Prior Publication Data

US 2013/0012946 A1    Jan. 10, 2013

(30) Foreign Application Priority Data

Jul. 5, 2011   (BE) .................................... 2011/0410

(51) Int. Cl.
| | |
|---|---|
| *A61B 17/56* | (2006.01) |
| *A61B 17/16* | (2006.01) |
| *A61B 17/17* | (2006.01) |
| *A61B 17/34* | (2006.01) |
| *A61B 10/02* | (2006.01) |

(52) U.S. Cl.
CPC .............. *A61B 17/56* (2013.01); *A61B 10/025* (2013.01); *A61B 17/16* (2013.01); *A61B 17/1615* (2013.01); *A61B 17/1633* (2013.01); *A61B 17/17* (2013.01); *A61B 17/3472* (2013.01); *A61B 17/1637* (2013.01); *A61B 2010/0258* (2013.01)

(58) Field of Classification Search
CPC ..................... A61B 10/025; A61B 2010/0258; A61B 17/16; A61B 17/1615; A61B 17/1633; A61B 17/1637; A61B 17/17; A61B 17/3472
USPC .......................... 606/79, 80, 86 R; 408/56, 59
See application file for complete search history.

(56) References Cited

U.S. PATENT DOCUMENTS

| | | | | |
|---|---|---|---|---|
| 4,456,010 A | * | 6/1984 | Reimels et al. ................ | 606/173 |
| 5,423,823 A | * | 6/1995 | Schmieding .............. | A61F 2/08 606/179 |
| 5,484,437 A | * | 1/1996 | Michelson ................... | 606/86 A |
| 5,489,307 A | * | 2/1996 | Kuslich .............. | A61B 17/1757 128/898 |
| 5,733,076 A | * | 3/1998 | Basteck .......................... | 408/59 |
| 6,071,284 A | * | 6/2000 | Fox .................... | A61B 10/0233 606/102 |
| 6,200,319 B1 | * | 3/2001 | Storer et al. ..................... | 606/79 |
| 6,267,763 B1 | * | 7/2001 | Castro ......................... | 606/86 A |
| 8,292,961 B2 | * | 10/2012 | Osman ........................ | 623/17.12 |
| 2004/0030343 A1 | * | 2/2004 | Kurc ............................... | 606/80 |
| 2004/0082957 A1 | * | 4/2004 | Stephen et al. ................. | 606/80 |
| 2006/0052790 A1 | * | 3/2006 | Miller ............................. | 606/80 |
| 2009/0228012 A1 | * | 9/2009 | Gangji et al. .................. | 606/80 |
| 2009/0275949 A1 | * | 11/2009 | Zwirnmann .................... | 606/80 |
| 2010/0114098 A1 | * | 5/2010 | Carl ............................... | 606/80 |
| 2010/0298832 A1 | * | 11/2010 | Lau et al. ....................... | 606/80 |
| 2011/0071578 A1 | * | 3/2011 | Colesanti et al. ............. | 606/305 |
| 2012/0191095 A1 | * | 7/2012 | Burger et al. ................. | 606/80 |

FOREIGN PATENT DOCUMENTS

| | | |
|---|---|---|
| EP | 1421907 A1 | 5/2004 |
| EP | 1 949 858 A1 | 7/2008 |
| FR | 22 625 429 A1 | 7/1989 |
| GB | 2 164 277 A | 3/1986 |
| WO | 97/16118 A1 | 5/1997 |

OTHER PUBLICATIONS

European Search Report dated May 26, 2015, for EP 12004406.0.

* cited by examiner

*Primary Examiner* — Larry E Waggle, Jr.
(74) *Attorney, Agent, or Firm* — Bacon & Thomas, PLLC

(57) ABSTRACT

Combination of a bone drill and a sleeve, whereby the combination comprises a receiving space for bone chips between the sleeve and the bone drill when the bone drill is inserted in the sleeve

12 Claims, 2 Drawing Sheets

COMBINATION OF A BONE DRILL AND A SLEEVE

FIELD OF THE INVENTION

Collecting bone tissue is a medical procedure that is carried out routinely. A distinction is made between the removal of a cytological sample (only bone marrow aspirate) in order to examine the effects of the bone marrow. Malignant cells can also be detected in this way.

BACKGROUND

To enable a histological assessment, however, a tissue sample of a single piece is required. Three variants are distinguished here. The taking of bone marrow, soft tissue or hard tissue.

Bone marrow is successfully removed with a hollow tube that can have many variants. Soft tissue from bone (e.g. in the event of malignant soft tissue) is done by a soft tissue biopsy system.

But to take a tissue sample that only consists of bone tissue, such as for example from the cortex of the bone or a tumour that consists purely of bone, a bone drill, also called a bone drill needle, is required.

The known bone drills generally only yield small tissue fragments, or scrapings, that present little coherence. As a result, it is difficult to determine the structure of the bone.

Improvements are known from FR 2.625.429 and GB 2.164.277 for example, that describe bone drills that are tubular and thereby have an internal cavity in which a larger, more or less intact, tissue sample can be located, so that a high-quality examination of the bone can be done.

However, the known bone drills have the disadvantage that when implementing a bone biopsy, bone chips or bone flakes are formed. These can spread in the body of the person undergoing the bone biopsy, which can lead to undesired complications, such as the spread of cancer tissue through the body.

SUMMARY

The purpose of the present invention is to provide a solution to the aforementioned and other disadvantages, by providing a combination of a bone drill and a sleeve, whereby the combination comprises a receiving space for bone chips between the sleeve and the bone drill when the bone drill is inserted in the sleeve.

The combination enables a relatively large piece of hard bone tissue to be collected in a safe and efficient way, because bone chips can be temporarily stored in the receiving space, until the biopsy procedure has been completed, after which the bone chips, together with the combination, can be removed from the body. Here the sleeve is preferably a cannula as is known in medical procedures.

In a preferred embodiment, the receiving space is entirely or partially formed by a recess in or a widening of the interior wall of the sleeve.

A traditional bone drill can be used here, whereby the receiving space in the specific case is formed by the recess or widening of the internal wall of the sleeve.

In a further preferred embodiment, the bone drill is provided with a recess in the wall to form the receiving space, whereby the receiving space has a medial wall that is formed by the external wall of the bone drill, and a lateral wall that is formed, by the internal wall of the sleeve.

The invention further relates to a kit for a bone biopsy that comprises a trocar, a stylet, and a combination as described above.

The invention further relates to a method for receiving pre-formed bone chips already formed that were formed when implementing a bone biopsy in which a bone drill is used in a sleeve, in which these bone chips are guided away by chip guides in the bone drill from the location where they were formed to a receiving space located between the bone drill and the sleeve:

Alternatively the invention can be described on the basis of the following clauses:

1: The present invention describes an embodiment of a biopsy instrument that is suitable for collecting bone tissue samples from very hard bone tissue;
2: The embodiment of clause 1 comprises a drill head with one or more sharp points to scrape off the bone tissue from the deeper lying layers.
3: The embodiment of clause 1 comprises an internal .space to receive a relatively intact bone tissue sample. This internal receiving space lies in the extension of the tube from which the bone drill needle is produced.
4: The embodiment of clause 1 contains chip guides that run from the drill head to a receiving space for bone chips. The form, length, inclination can present many variations.
5: The embodiment of clause 1 contains a recess in the wall as a receiving space for the bone chips. This receiving space has a medial wall, formed by an impression of the external wall of the bone drill needle. The lateral wall is formed from the internal wall of the cannula.
6: The cannula and the bone drill needle work operate conjunction for receiving bone chips, in order to avoid the bone chips being spread into the surrounding soft tissues.
7: The bone drill needle, for the purpose of a good operation, is aided by three other instruments: a stylet, a cannula and a trocar.
8: A stylet is added to the kit to remove the tissue samples that are received in the bone drill needle.
9: A complete kit for the bone biopsy comprises a trocar, a cannula, a bone drill biopsy needle and a stylet, with which the bone drill biopsy needle and cannula operate in conjunction.

BRIEF DESCRIPTION OF THE DRAWINGS

With the intention of better showing the characteristics of the invention, a preferred embodiment of a kit and a bone drill according to the invention is described hereinafter by way of an example, without any limiting nature, with reference to the accompanying drawings, wherein.

DETAILED DESCRIPTION OF VARIOUS EMBODIMENTS OF THE DISCLOSURE

Figure 1:
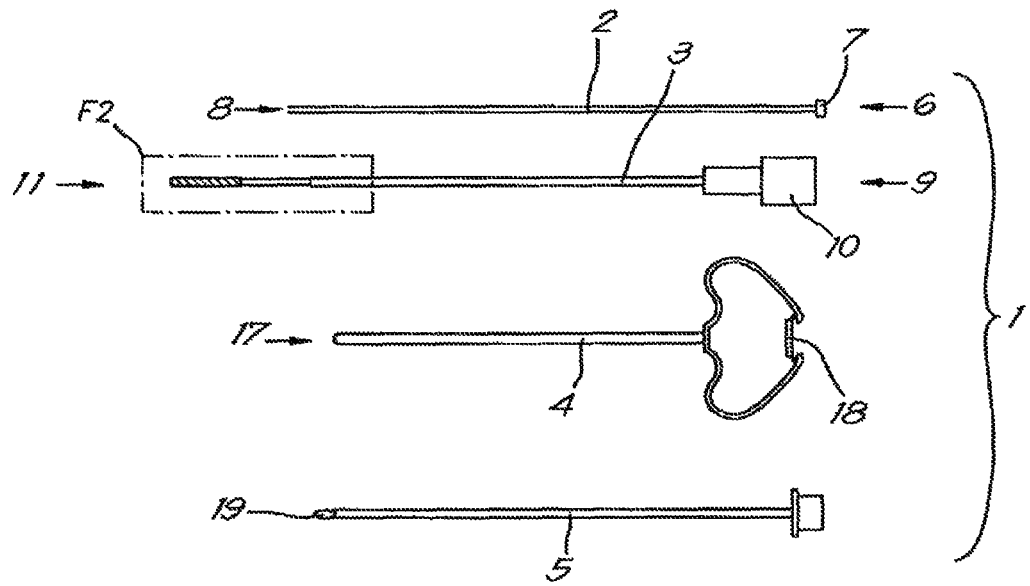
FIG. 1 shows a side view of a kit according to the invention.
Figure 2:
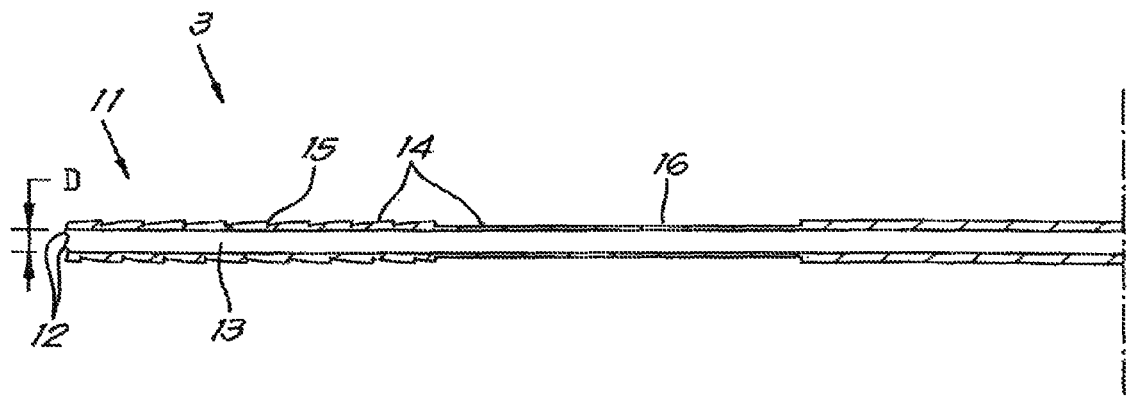
FIG. 2 shows a cross-section, on a larger scale, of the part designated by F2 in FIG. 1.
Figure 3:
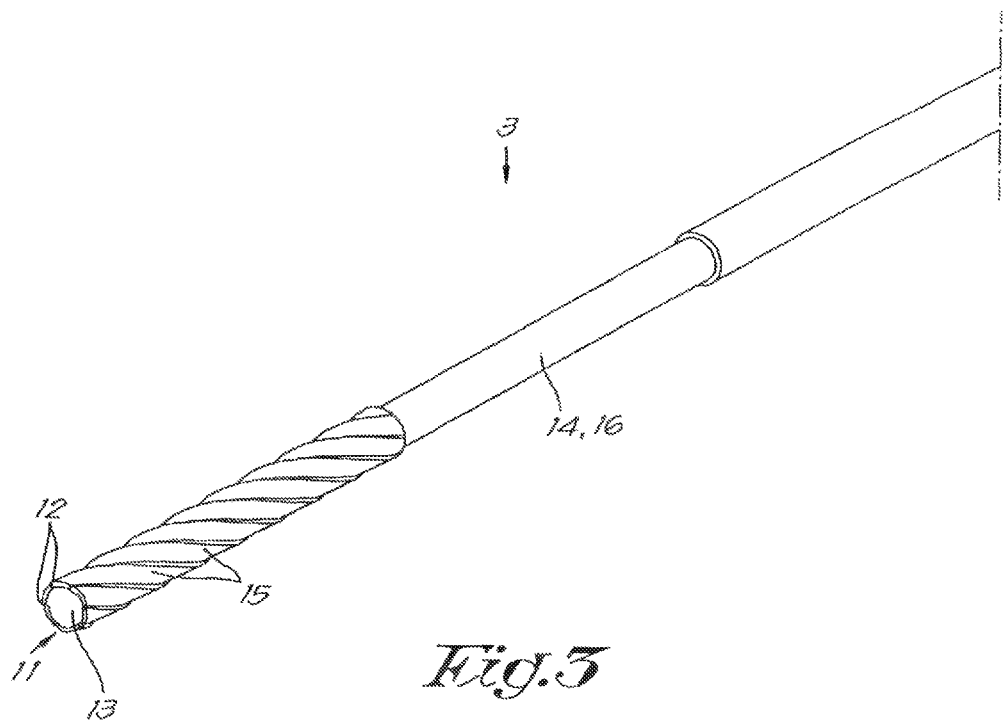
FIG. 3 shows a perspective view of the part of FIG. 2.
Figure 4:
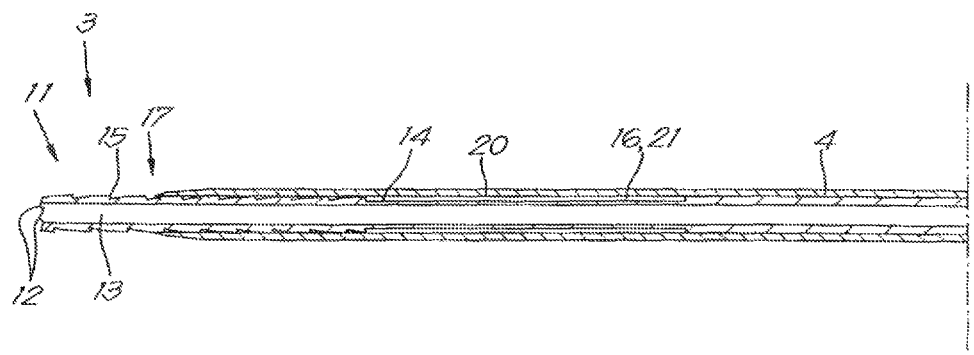
FIG. 4 shows the part of FIG. 2 in a configuration during use.

The bone biopsy kit 1 shown in FIG. 1 comprises four components, i.e. a stylet 2, a bone drill 3, a cannula 4 and a trocar 5.

The stylet 2 is a rod that can be produced from any material and with any dimensions. The proximal end 6 contains a button 7 to enable pressure on the stylet 2. The button 7 can be in various embodiments.

The distal end 8 of the stylet 2 is flat.

The proximal end 9 of the bone drill 3 has a button 10 with an axial opening that admits the stylet 2. At its distal end 11, the bone drill 3 has teeth that can be made from different materials.

The bone drill 3 has a sample space 13 that is created by the tubular structure of the bone drill 3. In the embodiment shown the sample space 13 is a single. chamber, although this is not necessary.

On its external wall 14 or external surface near its distal end 11, the bone drill 3 has a number of chip guides 15 that are in the form of a helical screw.

The length of the bone drill section that contains the chip guides is 2 cm in its preferred embodiment.

Proximally from the chip guides 15, and bordering them, there is a recess 16 that is formed by a receding external wall 14 of the bone drill 3. This is formed by an impression in the tube from which the bone drill is produced.

The length and depth of the recess 16 can of course be adjusted.

The internal diameter D of the bone drill 3 is somewhat larger than the external diameter of the stylet 2, so that the stylet 2 fits into the bone drill 3. The bone drill is preferably, but not necessarily, 1 centimeter shorter than the stylet 2.

The cannula 4 is a tubular element whose distal end 17 can be sloping or round. The edge of this distal end 17 is sharp in order to be able to penetrate and receive bone marrow.

The internal diameter of the cannula 4 is such that it closely fits the bone drill 3, but with such a clearance that the bone drill 3 can move freely. The length of the cannula is preferably but not necessarily such that, when the bone drill 3 is slid into the cannula 4 to a maximum, the bone drill 3 is two centimeters longer than the cannula 4, but any proportion can in principle be accepted.

The proximal section of the cannula 4 contains a button 18 that can be made in various embodiments. Centrally, the button 18 contains an opening with Luer connector for affixing an aspiration needle if need be. The opening provides enough space to admit the bone drill 3 and the trocar 5.

The trocar 5 is a rod or tube with a sharp point 19 that can be produced from different materials and in different lengths and diameters. The trocar 5 has a diameter that enables it to be slid into the cannula 4. In a preferred embodiment the trocar 5, when fully inserted in the cannula 4, is approximately 1 cm longer than the cannula, whereby the form of the point 10 is diamond-shaped with four sides.

Alternatively, the length can be equal to that of the cannula when both are of the beveled type. Other embodiments of the point of the combined cannula 4 and trocar 5 are possible.

The proximal section of the trocar 5 can be button-shaped whereby this button can click into the button. 18 of the cannula 4, in order to enable the combined movement of both components of the kit.

The operation of the kit 1 for taking a sample of hard bone tissue is simple and as follows.

After identifying the site of the tissue sample, for example by X-ray or CT scan, the skin is disinfected. The skin and dermis are anaesthetised. The periosteum is also anaesthetised.

Then an incision is made in the skin with a scalpel. The trocar 5 is placed in the cannula, and together they are inserted into the skin through the incision up to the periosteum.

The trocar 5 enables the cannula, through a relatively close fit in the cannula 4, to be brought under the skin up to the bone without tissue being taken into the cannula 4.

As soon as the cannula 4 is placed in the desired position, the trocar 5 is removed and replaced by the bone drill 3.

The internal wall 20 of the cannula 4 hereby acts as a guide for the bone drill 3. This internal wall 20 also forms the lateral wall, i.e. situated towards the outside, of a receiving space 21 for bone chips, that is formed by the recess 16 in the bone drill 3, whereby the external wall 14 of the bone drill 3 forms the medial wall, situated towards the inside, of the receiving space 21.

The bone drill 3 is then turned in the cortical bone or tumour until sufficient bone tissue is obtained in the sample space 13. Because the sample space 13 is surrounded by the bone drill 3, the integrity of the sample is assured.

The teeth 12 here are used to scrape off the bone in a circular motion and thereby enables the progress of the bone drill 3.

The chip guides 15 have a dual function here. Firstly they guide the bone splinters formed by the scraping to the receiving space 21. Moreover, after the bone drill has been taken a short distance into the bone, as a result of these chip guides 15 the bone drill develops a grip on the bone so that the person implementing the biopsy only has to exert a rotary and not a pushing movement to make the bone drill 3 progress.

The receiving space 21 receives the chips or scrapings from the teeth 12 during the procedure, and stores them temporarily, so that they cannot spread into the body.

After a sufficiently large sample has been collected, the bone drill 3 with bone sample is pulled out of the cannula 4. The bone tissue sample is then pushed out of the bone drill 3 by using the stylet 2.

The present invention is by no means limited to the embodiment described as an example and shown in the drawings, but such a bone drill needle can be realised in all kinds of variants, without departing from the scope of the invention.

The invention claimed is:

1. A combination of a bone drill and a sleeve, comprising:
a receiving space for bone chips between the sleeve and the bone drill when the bone drill is inserted in the sleeve,
wherein the bone drill is tubular and comprises an internal hollow sample space and a distal end having one or more sharp points configured to scrape off bone tissue, said internal hollow sample space located centrally and extending over a longitudinal length of the bone drill, wherein said internal sample space is configured to receive an intact single piece of bone tissue sample, wherein said intact single piece of bone tissue sample has a cylindrical shape,
wherein said receiving space is located remotely from said distal end, and
wherein the bone drill has chip guidance channels that extend from the distal end to the receiving space, wherein the chip guidance channels are in the form of a helical screw so that the chip guidance channels are configured to guide bone chips to the receiving space from the distal end.

2. The combination according to claim 1, wherein the sleeve comprises a cannula.

3. The combination according to claim 1, wherein the receiving space is entirely or partially formed by a recess or widening in an internal wall of the sleeve.

4. The combination according to claim 1, wherein the bone drill includes a recess in a wall thereof to form the receiving space, said receiving space including a medial wall that is formed by an external wall of the bone drill and a lateral wall that is formed by an internal wall of the sleeve.

5. A bone biopsy kit comprising a trocar, a stylet and the combination of a bone drill and a sleeve as recited in claim 1.

6. The combination according to claim 1, wherein the chip guidance channels are adjacent an internal wall of the sleeve.

7. The combination according to claim 1, wherein the internal hollow sample space for receiving an intact bone tissue sample within the bone drill is adjacent to the distal end of the bone drill.

8. The combination according to claim 1, wherein the chip guidance channels are formed by confined internal channels between the sleeve and the bone drill, where said confined internal channels have a helical shape.

9. The combination according to claim 1, wherein at least one of said end and chip guidance channels of the bone drill have a diameter configured in a way such that at least one of said distal end or chip guidance channels are insertable into the sleeve.

10. A method for implementing a bone biopsy in which a bone drill is used in a sleeve, comprising the steps:
   obtaining an intact single piece of bone tissue sample in an internal hollow sample space of the bone drill, said bone drill being tubular, wherein said internal hollow sample space is located centrally inside the bone drill and configured to receive the intact single piece of bone tissue sample, wherein said intact single piece of bone tissue sample has a cylindrical shape,
   guiding bone chips away from a distal end of the bone drill at a location where said bone chips were formed during obtaining of the intact single piece of bone tissue sample to a receiving space located between the bone drill and the sleeve using chip guidance channels, wherein said receiving space is located remotely from said distal end,
   wherein the distal end has one or more sharp points enabling scraping off bone tissue, and
   wherein the bone drill has the chip guidance channels that extend from the distal end to the receiving space, wherein the chip guidance channels are in the form of a helical screw so that the chip guidance channels guide the bone chips to the receiving space.

11. The method according to claim 10, further comprising the step of removing the single piece of bone tissue sample from the bone drill and examining the single piece of bone tissue sample.

12. A medical bone sampling instrument comprising:
   a bone drill and a sleeve,
   a receiving space for bone chips between the sleeve and the bone drill when the bone drill is inserted in the sleeve,
   wherein the bone drill is tubular and comprises an internal hollow sample space and a distal end having one or more sharp points configured to scrape off bone tissue and an opening, said internal hollow sample space located centrally and extending over a longitudinal length of the bone drill, wherein said internal sample space is configured to receive an intact single piece of bone tissue sample through said opening of the distal end, wherein said intact single piece of bone tissue sample has a cylindrical shape,
   wherein said receiving space is located remotely from said distal end, and
   wherein the bone drill has chip guidance channels that extend from the distal end to the receiving space, wherein the chip guidance channels are in the form of a helical screw so that the chip guidance channels are configured to guide bone chips to the receiving space from the distal end.

* * * * *